United States Patent [19]

Sun

[11] Patent Number: 5,437,866
[45] Date of Patent: Aug. 1, 1995

[54] HERBAL TREATMENT OF MALIGNANCY

[76] Inventor: Alexander S. Sun, 123 York St., 15K, New Haven, Conn. 06511

[21] Appl. No.: 855,025
[22] PCT Filed: Nov. 5, 1990
[86] PCT No.: PCT/US90/06376
   § 371 Date: Jun. 12, 1992
   § 102(e) Date: Jun. 12, 1992
[87] PCT Pub. No.: WO91/06306
   PCT Pub. Date: May 16, 1991

Related U.S. Application Data

[63] Continuation-in-part of Ser. No. 431,599, Nov. 3, 1989, abandoned.

[51] Int. Cl.[6] .............................................. A61K 35/78
[52] U.S. Cl. ........................ 424/195.1; 800/DIG. 23; Plt./100
[58] Field of Search ............. 424/195.1; 800/DIG. 23; Plt. 100

[56] References Cited

U.S. PATENT DOCUMENTS

| | | | |
|---|---|---|---|
| 4,461,760 | 7/1984 | Sugano et al. | 514/2 |
| 4,760,053 | 7/1988 | Labrie | 514/15 |

FOREIGN PATENT DOCUMENTS 2145528  4/1973  Germany ........................... 424/94.6

OTHER PUBLICATIONS

Sasaki S., "Antitumor Agents From Medicinal Plant," *Chemical Abstracts* (23 Jan. 1984) vol. 100, No. 4, abstract No. 26026w.

Bhakuni D. et al., "Medicinal Plants. III. Ericaceae and Other Families. Chemical Constituents of *Actinodaphne augustifolia, Croton sparsiflorus, Duabanga sonneratiodes, glycosmis mauritiana, Hedyotis auricularia, Lyonia ovalifolia, Micromelum pubescens, pyrus pashia* and *Rhodendron niveum*," *Chemical Abstracts* (6 Dec. 1971) vol. 75, No. 23, abstract No. 137510j.

Chem. Abst. 100(U):26026w, 1984.
Chem. Abst. 75(23):137510; 1971.

*Primary Examiner*—John W. Rollins
*Assistant Examiner*—Howard C. Lee
*Attorney, Agent, or Firm*—Morrison & Foerster

[57] ABSTRACT

A protocol using natural extracts which permit amelioration of malignancies in humans is disclosed. The protocol mandatorily includes an extract of *Lentinus edodes* and mung beans, and optionally further includes the combined extract of *Hedyotis diffusa* and *Scutellaria barbata*.

10 Claims, 4 Drawing Sheets

DAY AFTER INJECTION

DAY AFTER INJECTION

DAY AFTER INJECTION

UNTREATED    TREATED

HERBAL TREATMENT OF MALIGNANCY

This application is a continuation-in-part of Ser. No. 07/431,599, filed 3 Nov. 1989 and now abandoned.

TECHNICAL FIELD

The invention is related to treatments effective in treating malignancies. In particular, it concerns extracts of plants which, when used in a specified protocol, are effective against these conditions.

BACKGROUND ART

It is understood that malignancy is a highly refractory disease against which a number of treatments have been recognized in Western societies as at least palliative—including surgery, chemotherapy, radiation therapy and photodynamic therapy. However, although the mechanisms and etiology of the disease are incompletely understood, it is recognized that the victim of the disease is capable in many cases of marshalling indigenous defenses. Indeed, it is believed that the condition occurs because of the breakdown of these natural defenses.

Accordingly, materials which enhance the capability of the subject to mount its own defense are useful in treatment. The present invention describes such compositions and protocols.

DISCLOSURE OF THE INVENTION

The invention is directed to a protocol of administration of the combination of extracts of *Letinus edodes* plants, mung bean, *Hedyotis diffusa* (wild) and the herb *Scutellaria barbata*.

Thus, in one aspect, the invention is directed to a method of treating a subject afflicted with a malignant condition which method comprises daily administration of the combination of:

50 g dry weight of *Lentinus edodes*; and the cooked extract of about 50 g of softened mung bean; and on at least one day during the regimen, the cooked extract of 50 g of *Hedyotis diffusa* and 50 g of *Scutellaria barbata*, extracted together.

In preferred embodiments, all four extracts are administered daily.

MODES OF CARRYING OUT THE INVENTION

Figure 1A:
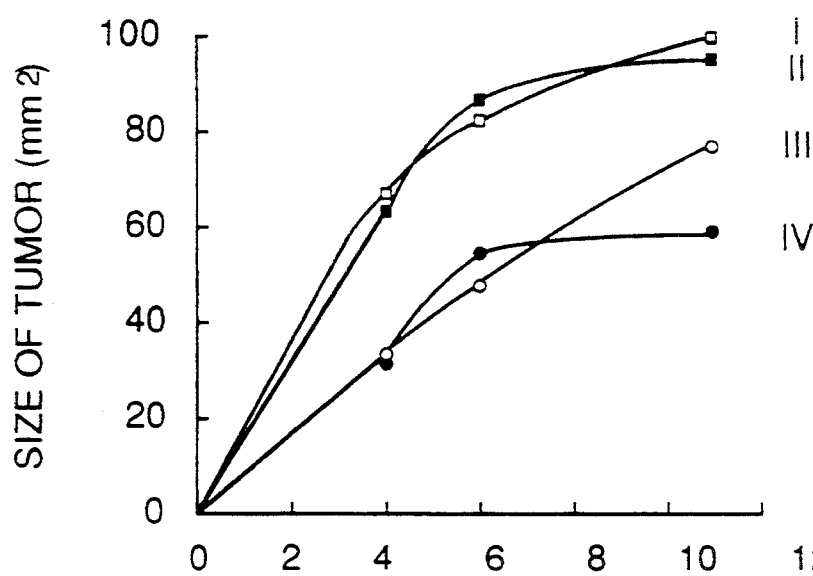
FIGS. 1A and 1B show the effect of the diet of the invention on tumor growth in murine model 1.

As used herein, "cooked aqueous extract" refers to an extract prepared by boiling the relevant plant or portion thereof in water, optionally containing additional materials for flavoring. The extract may be decreased in volume if desired.

Preferred methods for preparing the required extracts are as follows:

1. *Letinus edodes*: For about 50 g (dry weight) per day, the whole plant is macerated in a food processor and is cooked with meat or chicken as soup for at least 5 minutes at 100° C. The plant is known to contain several polysaccharides, which are known to stimulate natural killer cell activity.

2. Mung bean: About 50 g (dry weight) per day is prepared by boiling to soften the bean, and the whole bean is eaten. A boiled extract is, however, preferred. This is prepared by grinding the beans, e.g., in a coffee grinder and boiling at 100° C. for 5 minutes. Preferably, however, the cooked extract is used.

Mung bean is known to contain nucleases as well as protease inhibitors. Nucleases hydrolyze single-stranded DNA; when cancer cells proliferate, their DNAs change to single-stranded DNA first, which could be digested by mung bean nucleases. Proteases could facilitate metastasis of cancer cells. Mung bean protease inhibitors may have the effect of preventing cancer metastasis.

3. *Hedyotis diffusa* (wild): About 50 g (dry weight) is extracted for each daily amount. The herb should be washed with water, covered with water, and cooked together with 50 g of *Scutellaria barbata* (see paragraph 4), and 10 of the root of *Glycyrrhiazuralensis fisch* as a sweetener. This herb is known to inhibit the growth of tumor S-180, $U_{14}$ and L1 ascites. The herbs should not be eaten; only the soup should be drunk once or twice a day. The soup should be cooked down to the volume of a coffee cup.

4. *Scutellaria barbata*: This herb should be cooked with *Hedyotis diffusa* (wild). This herb is known to inhibit the growth of tumor S-180, ascites and T22.

The protocol can be administered orally as set forth above, and it should be noted that extracts 3 and 4 may be supplied on less than a daily basis. However, at least one administration of these extracts should be included in the protocol.

The continuance of the regimen of the invention, along with a proper balanced diet results in continued amelioration of malignancy. Further, the regimen is a suitable preparation for surgical treatment once solid tumors become isolated and encapsulated with respect to surrounding tissue and can more easily be removed.

The extracts are administered orally and can be prepared as foods of acceptable flavor and texture by methods generally known in the art. In general the amounts of material administered are in the range of those corresponding to the extracts of 25–200 g of the *Letinus edodes* and mung bean essential components, and similar amounts of the optional additives.

It is important to emphasize that the regimen must include an adequate diet in other respects to ensure that the subject can mount the requisite immune response.

The following examples serve to illustrate, but not to limit, the invention. The first 4 examples are the results in animal models. Example 5 provides data showing the efficacy of this protocol on four patients, two of whom had large cell adenocarcinoma of the lung with metastases to adrenal gland, lymph nodes and the brain, the other two of whom have renal cell carcinoma with metastases to lung and liver. All four patients were known to be terminal.

Introduction: Procedures for Examples 1–4

Induction of Antitumor Immunity in Murine Tumor Models

Two in vivo models were used.

Model I: A/J (H-2$^a$) mice, 6–8 weeks old, maintained in a clean, pathogen-free environment were divided into groups of four mice. Mice in each group were consistently fed a diet to be tested. Groups were caged separately and were started on the test diet three days before inoculation with tumor. Acidified water was provided ad libitum. For tumor inoculation, $10^5$ Sarcoma S1509a cells were administered subcutaneously into the shaved dorsum. In controls, these cells are known to grow rapidly and to kill the mice in an average of 27 days after inoculation. The growth of the tumors is determined every few days for 12 days after inoculation by measuring the surface area (mm$^2$) of the resultant growing tumor using Vernier calipers.

(A similar experiment was conducted using one hundred Sarcoma cells per mouse, with fifteen mice in each group.)

Model II: Balb/c mice were divided into groups of five mice each and inoculated with Line 1 lung carcinoma cells, a spontaneous murine tumor deficient in class 1 antigen expression and highly metastatic in vivo. Ten thousand cells were injected per mouse subcutaneously, and the size of the tumor was measured in volume (mm$^3$) using Vernier Calipers.

EXAMPLE 1

Using Model I set forth in the Procedure above, Groups I and II were control groups and were fed either a preparation made by mixing 800 g commercial lab chow powder with 800 ml water made into pellet form and air-dried (Group I) or commercial solid lab chow pellets (Group II). In the experimental groups, Group III received a diet prepared from 640 g of lab chow powder, 80 g of *Lentinus edodes* powder, and 80 g of mung bean powder, supplemented with extract from 150 g of *Hedyotis diffusa* (wild) and 150 g of *Scutellaria barbata*, and made into pellet form and air-dried.

Figure 1B:
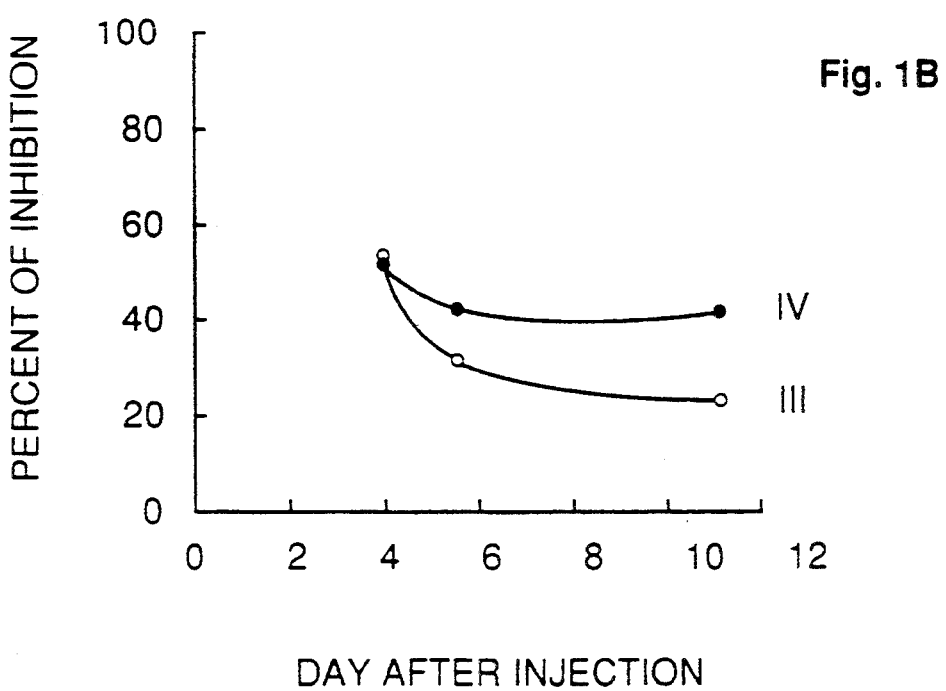

Group IV received a diet obtained by mixing 640 g of lab chow powder, 80 g of *Lentinus edodes* powder and 80 g of mung bean powder, 800 ml of distilled water, pelleted and air-dried. Tumors were measured on the fourth, sixth and eleventh day after injection of tumor cells with the results shown in FIGS. 1A and 1B. As shown in the figure, the increase in tumor size for the test groups was appreciably less than controls; the percentage inhibition computed from the results of FIG. 1A is shown in FIG. 1B. As there shown, the percent inhibition of tumor growth rate as compared to Group I on the fourth, sixth and eleventh days was 49.3%, 41% and 39% for Group III, and 50.8%, 32.5% and 24% for Group IV.

EXAMPLE 2

Figure 2A:
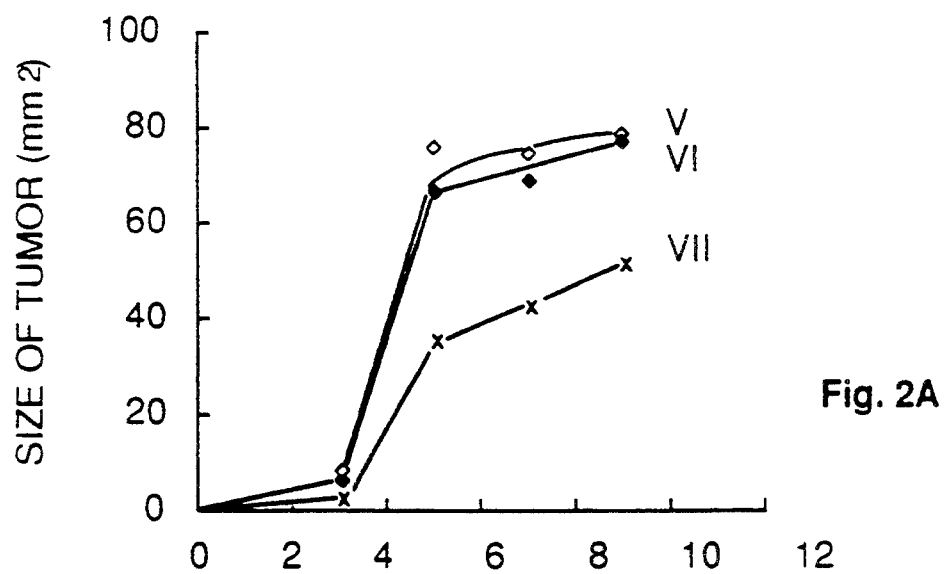
FIGS. 2A and 2B show the results, in an additional experiment, of the effect of the invention diet on tumor growth in murine model 1.
Figure 2B:
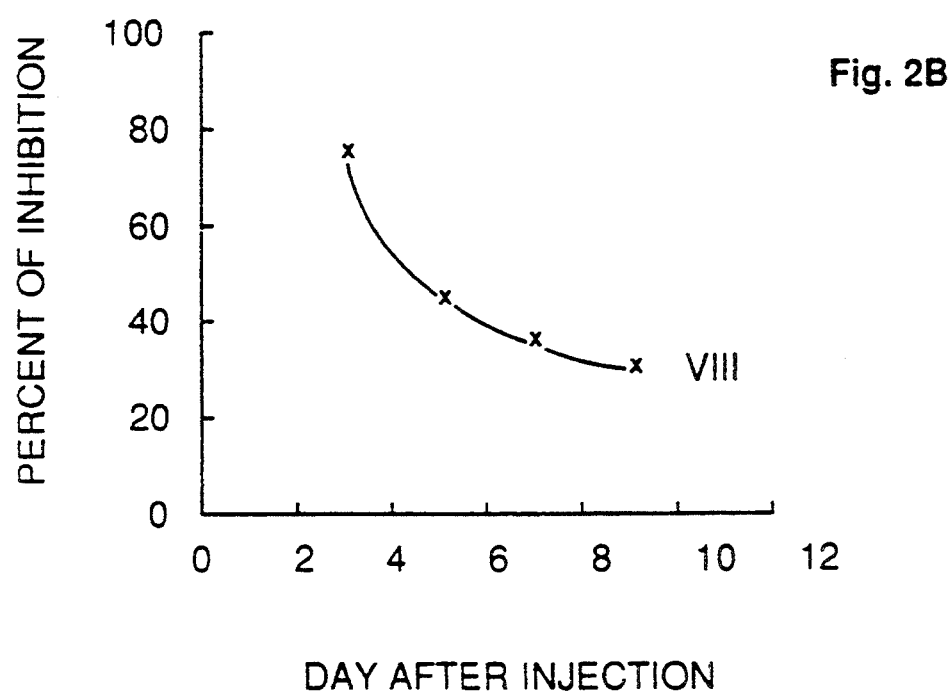

Using the models of the Procedure, three groups of mice were tested. Groups V and VI were controls corresponding to Groups II and I of Example 1, respectively. Group VII was fed a diet prepared with 640 g of lab chow powder, mixed with 400 ml boiling water extract of 80 g of mung bean powder and 400 ml boiling water extract of 80 g of *Lentinus edodes*. The results are shown in FIGS. 2A and 2B.

As shown in the figures, tumor growth was inhibited, as measured on days 3, 5, 7 and 9 in the test groups versus the controls. FIG. 2B shows the percent inhibition of Group VII as compared to Control Group VI. The percent inhibition on day 3 was 75.8%; 46.7% on day 5; 37.7% on day 7; and 30.1% on day 9.

EXAMPLE 3

The Model 1 of Procedure was used but using only 100 tumor cells per inoculum to determine whether the antitumor effect is operable when adaptive immunity is not yet active. Mice were examined each day after injection of cells. No definite tumors were observed at first, but after three weeks, tumors developed in 11 of the 15 mice in the control group, but in only 1 of the mice in a test group which received in the same manner as Group VI described in Example 2.

EXAMPLE 4

Using the Model II of Procedures, Control Group I was fed commercial lab chow mixed with water, made into pellet form and air-dried. Test Group II was fed a diet prepared from 720 g lab chow mixed with a boiling water extract from 80 g of mung bean, made into pellet form and air-dried. Test Group III was fed a diet prepared from 720 g lab chow mixed with boiling water extract from 80 g of *Lentinus edodes* made into pellet form and air-dried. Test Group IV was fed a diet made from 640 g of lab chow powder mixed with a boiling water extract from 80 g of *Lentinus edodes* and from 80 g of mung bean made into pellet form and air-dried.

Figure 3A:
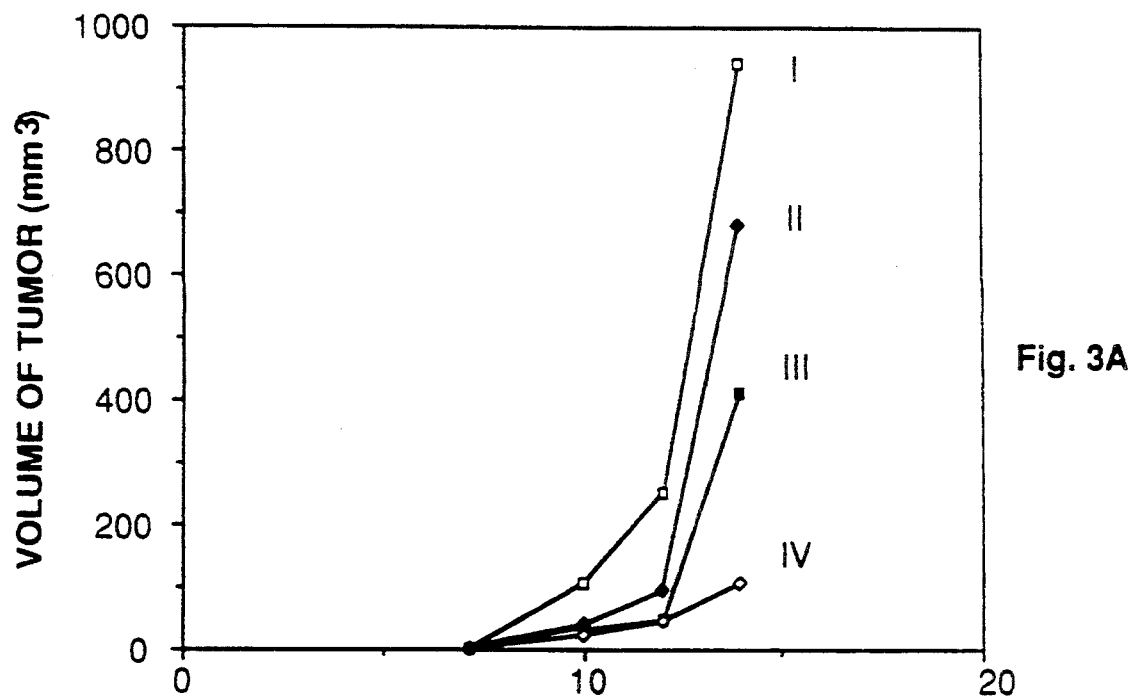
FIGS. 3A and 3B show the effect of the invention diet on tumor growth in murine model 2.
Figure 3B:
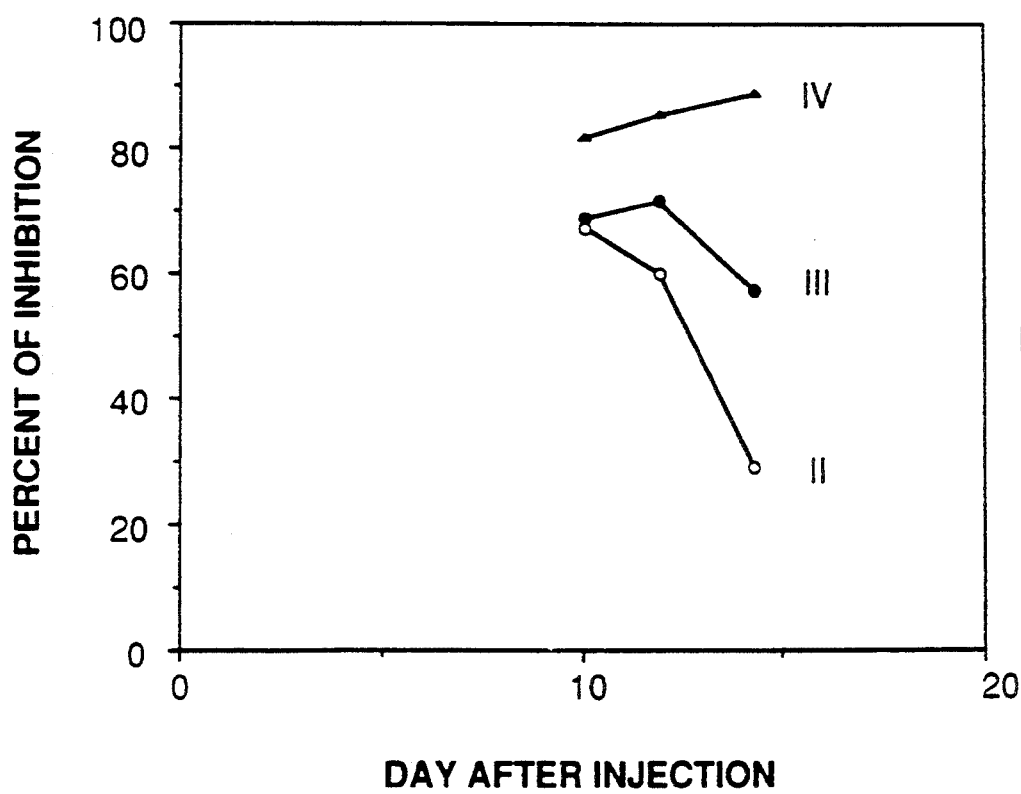
Figure 4:
FIG. 4 shows a comparison of the tumor size in treated and untreated mice.

The results of this model are shown in FIG. 3. The results show that the tumor volume in animals receiving the test diets were dramatically reduced, as measured by the volume of the tumor, measured on days 7, 10, 12 and 14. The inhibition in Group IV is dramatically different from that of Groups II and III, as shown in FIG. 3B. The percent inhibition obtained in Group IV increases over the measurement period from 76% to 82% to 85%. As shown in FIG. 4, the difference in tumor size in Groups I and IV is visible to the naked eye. Further, the tumors are encapsulated and moved away from the surrounding tissue.

EXAMPLES 5

Human Patients

Patient 1

Mrs. A: Female; Date of Birth: Jan. 2, 1916. Events and Dates:

1. October 1984: Sputum with blood.
2. November 1984: X-ray shows a shadow in the lower right lung; Dr. Ming Chuang, Mount Sinai School of Medicine, New York.
3. Dec. 21, 1984: First bronchoscopy biopsy found no evidence of tumor.
4. Jan. 1, 1985: Second bronchoscopy biopsy found poorly differentiated large cell carcinoma.
5. Jan. 24, 1985: The patient underwent lobectomy of right lower lobe of the lung at Mount Sinai Hospital, New York. Her tumor was identified as giant spindle cell of adenocarcinoma of the lung. A lymph node in the subcarinal region was found to have the same type of tumor. Thus, she was considered to have Stage III large cell adenocarcinoma of the lung, which is known not to respond to any chemotherapy or any radiotherapy. None of such patients could live more than a year.
6. Apr. 17–Aug. 7, 1985: Since the chance of metastasis of Stage III adenocarcinoma of the lung is high, and there was no better treatment, upon the advice of an attending physician, the patient was treated with adjuvant chemotherapy even though this treatment is known not to be effective for this type of tumor. The patient was treated with methotrexate, Adriamycin, Cytoxan, and CCNU. She was treated on April 17, May 15, June 30, July 10 and August 7.

7. Sep. 3, 1985: A tumor was discovered in the patient's left adrenal gland.
8. Sep. 7–Nov. 3, 1985: Since there was no better treatment, the patient, was treated with 1500 rad of radiotherapy which is also known to be ineffective. The tumor did not decrease in size (5×4×4 cm).
9. Sep. 3–Nov. 10, 1985: The patient began to be treated with four Chinese herb medicines—mung beans, black mushroom (*Letinus edodes*), *Hedyotis diffusa* (wild) Roxb, and *Scutellaria barbata* Don.
10. Nov. 12, 1985: She was admitted to Junkankika Hospital, Kumamoto, Japan. On November 17, a CT scan showed the tumor in her adrenal gland was 5.8×3.8×6 cm.
11. Nov. 13–Dec. 8, 1985: Fresh black mushroom had been included in her diet when she was in Japan until her surgery on Dec. 9, 1985.
12. Nov. 18, 1985: 1.7 ml of oil smancs in Lipiodol was injected into her tumor via the renal artery. Most parts of the smancs did not get into the tumor.
13. Nov. 11, 17, 18, 19, 20, 1985: IV injection of smancs was administered at a dosage of 2 mg/day.
14. Nov. 22, 23, 26, 27, 30 and Dec. 1, 1985: IV injection of smancs was administered at 0.5 mg/day. A side-effect of the smancs was obvious (nausea) and smancs treatment was stopped.
15. Dec. 9, 1985: An adrenalectomy was performed. Tumor size was 6.6×4.2×3.1 cm and the tumor was well encapsulated and was diagnosed as large cell adenocarcinoma.
16. Dec. 12–20, 1985: Fresh black mushroom had been included in her diet
17. Jan. 1, 1986-present: Fresh black mushroom and mung bean have always been included in her diet three to four times a week.
18. Apr. 1–Jul. 30, 1986: Adjuvant chemotherapy with smancs was injected intravenously. (One cycle included 0.5 mg/day for seven days and rest for seven days. Four cycles were administrated. Rest for one month and started another four cycles.)
19. The patient has had no detectable tumor since her adrenalectomy on Dec. 9, 1985. Six years have passed since the first symptom of her tumor.

Patient 2

Mr. B: Male; Date of Birth: January, 1920. Events and Dates:

1. Oct. 9, 1980: The patient underwent radical nephrectomy (right). The tumor mass was about 20×20×15 cm over the lower part of the right kidney and diagnosed as renal cell carcinoma.
2. Jan. 31, 1986: Exploratory thoracotomy and wedge resections were performed and found: 1. A firm tumor about 2 cm over the lingula segment of LUL. 2. Two firm tumors, one over the basal part about 2.5 cm and the second over the central part of the LRL, and the third small one about 0.5 cm over the superior surface of LRL. 3. A small adhesion was noted over the LUL of lung. Wedge resections of the peripheral tumors and the enucleation of the central tumor were performed. All five tumors showed metastatic renal cell carcinoma, which is composed of both clear and granular tumor cells.
3. Dec. 12, 1986: Exploratory thoracotomy with multiple enucleation of tumors was performed. Multiple metastatic small tumors within the parenchyma and lung surface, a total of 28 tumors (14 on RUL, 6 on RML and 7 on RLL), were removed.
4. Aug. 31, 1987: Left thoracotomy with enucleation of 12 metastatic tumors was performed. Two big tumors (2×2 cm) over LUL, 8 small tumors over LUL and 3 small tumors over LLL. A picture of metastatic renal cell carcinoma was found.
5. Jan. 8, 1988: Two nodules were identified by CT scan over the right hepatic lobe, one in the anterior segment and another one in the posterior segment. Another 26 nodules (which is patient's statement and no pathological records have been seen) were found in patient's lung.
6. Feb. 1, 1988: The patient has been treated with two Chinese herbs (mung bean and black mushroom) and smancs since February 1988 with no side-effects nor any discomfort.
7. August 1988–January 1989: No tumor was found in the patient.
8. January 1989: The patient stopped taking mung bean and black mushroom, but continued smancs IV injections (1 mg every other day).
9. Jul. 20, 1989: Two tumors were found in the patient's lung and the patient resumed including mung bean and black mushroom in his diet.
10. Aug. 20, 1989-present: The patient has no detectable tumor and was told to stop smancs treatment. He continues including mung bean and black mushroom in his diet. He has no detectable tumor at present.

Patient 3

Mr. C was born in 1940. He underwent a right nephrectomy in September of 1986 for renal cell carcinoma. The tumor invaded the renal vein. In February of 1987 CT scan of the chest revealed a nodule approximately 1 cm in diameter in the right lower lobe of his lung. On Jul. 30 of 1987, the patient underwent a lobectomy of the right lower lung and dissection of the right hilium. The lung lesion was histologically a clear cell adenocarcinoma, typical of renal cell carcinoma. Several of the submitted hilar lymph nodes contained metastatic carcinoma. On Aug. 5, 1987, his doctor stated that the probability of cure at this stage appears quite unlikely and that postoperative irradiation to the hilar-mediastinal areas may not significantly influence the course of the disease. On Feb. 29, 1988, an enhanced computed tomography of the thorax, abdomen and pelvis was performed. The possibility of early retroperitoneal metastatic disease was noted. Beginning from Aug. 3 of 1988, the patient has been treated with smancs and two Chinese herbs (mung bean and black mushroom) with no side-effects nor any discomfort. He is in excellent physical condition and has had no detectable tumor as of October of 1989. In January 1990, the patient took the wrong kind of black mushroom. In March 1990, an enlarged lymph node was discovered, apparently due to a change in treatment. In April 1990 patients resumed using the right kind of black mushroom. In July 1990, a tumor adjacent to the inferior vena cava was removed. The tumor was confined in a well-defined capsule. No other tumor was detected as of October 1990.

Patient 4

Mrs. D was born in 1913. On Mar. 4, 1986, the patient underwent a lobectomy of the right upper lung. The tumor was identified as large cell adenocarcinoma of the lung. On Oct. 10, 1986, multiple metastatic lesions were found by CT scan in her cortico-white junction over the left frontal and parietal lobes of her brain with post-contrast enhancement and peripheral edema. She has been treated with two Chinese herbs (mung bean and black mushroom) and smancs since Dec. 13, 1986, with loss of appetite. In March of 1987, CT scan revealed that all of her three metastatic brain tumors disappeared. The patient was treated with smancs and the two Chinese herbs continuously until August of 1987. No tumor was detected then. General weakness of the patient was evident, probably due to the loss of appetite and malnutrition, a side-effect of smancs found with some patients. In September of 1987, the patient went back to Taiwan. However, soup got into her lung when she was drinking soup and coughing. She had pneumonia and was treated with an antibiotic (the name has to be identified) which has the side-effect of destroying platelets. The patient died from low platelets on Dec. 24, 1987. Autopsy was not performed because of objection by the family members. The patient had no detectable tumor as shown with CT scan in late August of 1987, a month before she died of side effects of an antibiotic that depletes platelets administered to treat pneumonia.

I claim:

1. A method to ameliorate at least one effect of malignancy in humans which method comprises
administering to a subject in need of such treatment an anti-malignancy effective amount of a boiling water extract of *Letinus edodes* and an anti-malignancy effective amount of extract of mung bean, said extracts being administered periodically for a time sufficient to achieve amelioration.

2. The method of claim 1 which further includes administering to said subject, in combination with said extracts a composition which comprises an anti-malignancy effective amount of a boiling water extract of approximately equal weights of *Hedyotis diffusa* and *Scutellaria barbata*.

3. The method of claim 1 wherein said anti-malignancy effective amount is an extract of 25–200 g of *Letinus edodes* and of mung bean per day.

4. The method of claim 1 wherein the malignancy is a carcinoma.

5. The method of claim 1 wherein the malignancy is a solid tumor and the administering is performed before surgery.

6. The method of claim 1 wherein said periodic administration is conducted daily, or three to four times a week.

7. A method according to claim 1 wherein said extract of *Letinus edodes* and said extract of mung beans are administered as a single composition.

8. A method according to claim 2 wherein said extract of *Letinus edodes*, said extract of mung beans and said extract of *Hedyotis diffusa* and *Scutellaria barbata* are administered as a single composition.

9. A composition useful for ameliorating at least one effect of malignancy in humans, which composition comprises an anti-malignancy effective amount of a boiling water extract of 25–200 g *Letinus edodes* and an anti-malignancy effective amount of extract of 25–200 g mung beans for administration in one day.

10. A composition according to claim 9 further comprising an anti-malignancy effective amount of a boiling water extract of approximately equal weights of about 25–200g *Hedyotis diffusa* and *Scutellaria barbata* for administration in one day.

* * * * *